US00PP15095P2

(12) United States Plant Patent
Heims

(10) Patent No.: US PP15,095 P2
(45) Date of Patent: Aug. 24, 2004

(54) LOBELIA PLANT NAMED 'WHITE CANDLES'

(50) Latin Name: *Lobelia siphilitica*
Varietal Denomination: White Candles

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 37 days.

(21) Appl. No.: 10/611,579

(22) Filed: Jun. 30, 2003

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—Klarquist Sparkman, LLP

(57) ABSTRACT

A new and distinct cultivar of *Lobelia siphilitica* plant characterized by a dwarf habit and multiple short flowering stems of numerous white flowers.

1 Drawing Sheet

Botanical classification: *Lobelia siphilitica.*
Variety denomination: 'White Candles'.

BACKGROUND OF THE INVENTION

The present invention relates to a new and distinct *Lobelia siphilitica* and given the cultivar name 'White Candles'. Lobelia is in the family Lobeliaceae. This new cultivar originated from several generations of open pollinations and selections among select dwarf *Lobelia siphilitica* compact (proprietary plants).

This plant is unique due to its combination of dwarf habit and congested heads of white flowers. It is characterized by the following:

1. Dwarf habit.
2. Numerous white flowers.
3. Strong, short flowering stems that don't fall over.

The new variety has been reproduced only by asexual propagation (cuttings and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a two-year-old Lobelia 'White Candles' growing in the trial fields in August in Canby, Oreg.

DETAILED PLANT DESCRIPTION

The following is a detailed description of the new Lobelia based on observations of a two-year-old specimen grown in the field in Canby, Oreg. The color descriptions are all based on The Royal Horticultural Society Colour Chart.

Botanical name: *Lobelia siphilitica.*
Cultivar name: 'White Candles'.

Parentage: *Lobelia siphilitica* compact forms — open pollinated.

Plant:
- *Type.*—Herbaceous perennial.
- *Hardiness.*—USDA Zones 4 to 9.
- *Size.*—32 cm wide and 40 cm. tall.
- *Form.*—Basal clump.

Leaf:
- *Type.*—Simple.
- *Shape.*—Obovate.
- *Arrangement.*—Rosette to alternate up flowering stem.
- *Blade length.*—5 to 8 cm.
- *Blade width.*—3 to 4.2 cm.
- *Margins.*—Irregularly serrulate.
- *Apex.*—Acute to obtuse.
- *Base.*—Attenuate.
- *Texture.*—Smooth.
- *Surface.*—Matte.
- *Vestiture.*—Sparsely pubescent.
- *Venation.*—Pinnate.
- *Petiole length.*—2 to 4 cm.
- *Color.*—Topside — Green 137A. Bottom — Closest to Green 138B.

Inflorescence:
- *Type.*—Terminal raceme.
- *Peduncle.*—Height: 40 cm. Diameter: 4 to 7 mm. Vestiture: Glabrous to sparsely pubescent. Color: Yellow Green 144A.
- *Pedicel.*—Length: 0.5 cm. Texture: Sparsely pubescent. Color: Yellow Green 144B.
- *Flower number.*—80 to 100 per raceme with secondary flowers later in the leaf axils.

Flower bud:
- *Size.*—2.4 cm. deep and 0.8 cm. wide.
- *Shape.*—Oblong. Tube-like on bottom ⅔ then constricted and top ovoid with an acute tip.
- *Vestiture.*—Sparsely pubescent.
- *Color.*—White with a creamy tip, White 155D with Yellow White 158B.

Flower:
- *Type.*—Zygomorphic.
- *Shape.*—Bilabiate.
- *Size.*—2.5 cm deep and 1.2 cm. wide.

*Corolla.*—Slit ⅞ down on the upper side between the two upper lobes, upper lobes recurve and are 11 mm long and 4 mm wide at the base and with acuminate tips. Lower three lobes close together and 1.1 cm long and 5 mm wide. Tube is 16 mm long and 8 mm wide.

*Texture.*—Satiny.

*Color.*—White 155D with Yellow White 158B at the very tips of the lobes.

*Calyx.*—5 deeply cut acuminate lobes, linear lanceolate, parted to corolla base, lobe sides revolute.

*Calyx lobe size.*—12 mm deep and 2.5 mm wide at base.

*Calyx color.*—Yellow Green 144A with dark tips, Greyed Purple 187B.

*Pistil.*—2 cm. long, Yellow Green 145B.

*Stamen number.*—5 in a column around the stigma, White 155D.

*Filament length.*—16 mm.

*Anther size before dehiscing.*—0.5 cm.

*Pollen color.*—Light cream, Yellow 11C.

*Bloom period.*—July and August in Canby, Oreg.

*Fragrance.*—None.

Fruit:

*Number.*—50 to 100 per raceme.

*Shape.*—Ovoid.

*Size.*—8 mm wide and 8 mm deep.

*Type.*—Dehiscent capsule.

*Color.*—Tan, Grey Brown 199D.

Seed:

*Size.*—0.05 mm.

*Color.*—Black 202A.

*Shape.*—Ovoid.

*Fertility.*—Fertile.

Pest resistance: No observed pest resistance.

Disease: Lobelia are susceptible to rust, smut, and leaf spots. None of these have been observed on plants grown under commercial conditions in Canby, Oreg.

COMPARISONS TO SIMILAR LOBELIA

Compared to the species, *Lobelia siphilitica* 'White Candles' is much more compact and with many more flowers congested together on the flowering stems. The flowers are white rather than blue, there are also more flowering stems than usual.

Compared to *Lobelia siphilitica* compact forms used for the open pollination, this new variety is white rather than blue, and has superior flower number.

I claim:

1. A new and distinct cultivar of *Lobelia siphilitica* plant substantially as shown and described, characterized by a dwarf habit and multiple short flowering stems of numerous white flowers.

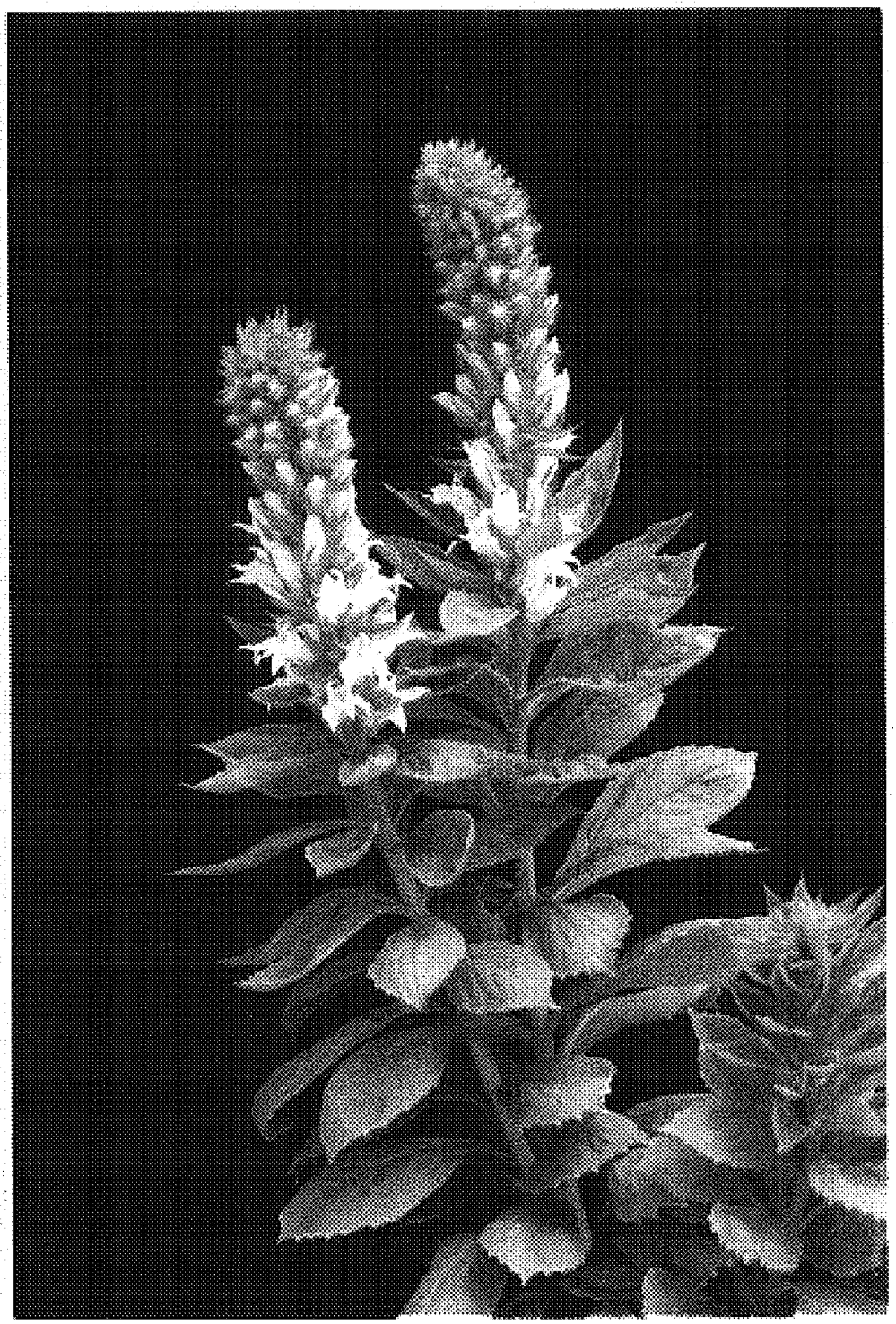

* * * * *